United States Patent [19]
Naujokas et al.

[11] Patent Number: 5,654,470
[45] Date of Patent: Aug. 5, 1997

[54] RECOVERY OF COMPONENTS FROM POLYESTER RESINS

[75] Inventors: Andrius Algimantas Naujokas, Webster; William James Gamble, Rochester, both of N.Y.

[73] Assignee: Eastman Kodak Company, Rochester, N.Y.

[21] Appl. No.: 687,819

[22] Filed: Jul. 26, 1996

[51] Int. Cl.$^6$ .................................................. C07C 67/60
[52] U.S. Cl. ........................... 560/78; 562/483; 562/485; 568/854
[58] Field of Search ...................... 560/78; 562/483, 562/485; 568/854

[56] References Cited

U.S. PATENT DOCUMENTS

| | | | |
|---|---|---|---|
| 2,219,996 | 10/1940 | Livingston | 260/343 |
| 2,868,830 | 1/1959 | Weedman | 260/475 |
| 3,621,506 | 11/1971 | Armstrong et al. | 15/246 |
| 3,836,573 | 9/1974 | Schreiber et al. | 260/475 |
| 4,315,541 | 2/1982 | Murata et al. | 165/94 |
| 5,051,528 | 9/1991 | Naujokas et al. | 560/78 |

*Primary Examiner*—Samuel Barts
*Attorney, Agent, or Firm*—Joshua G. Levitt

[57] ABSTRACT

There is described a process for the depolymerization of polyethylene terephthalate into component monomers at ambient pressure. Monomer solids that deposit during cooling, as part of the recovery operation, are removed using a scraped wall heat exchanger.

5 Claims, 1 Drawing Sheet

RECOVERY OF COMPONENTS FROM POLYESTER RESINS

FIELD OF INVENTION

This invention relates to a process for recovering ester and glycol components from condensation-type polyester resins and to apparatus for carrying out that process.

BACKGROUND OF THE INVENTION

Polyester resins have found widespread use in varied applications. Polyesters such as polyethylene terephthalate are used in photographic film, in magnetic tape, in fibers, and in food and beverage containers. Various methods have been disclosed for the depolymerization of such resins into their component monomers, such as ethylene glycol and terephthalic acid or derivatives thereof, so that they can be reused.

Some of these methods are described in such patents as U.S. Pat. Nos. 3,037,050, 3,321,510, 3,884,850, 3,907,868, 4,163,860, 4,578,502, 4,620,032, 4,876,378 and 5,095,145, and in European Published Patent Application 0 484 963 published May 13, 1992.

A particularly useful technique for recovering polyester monomers is described in Naujokas et al. U.S. Pat. No. 5,051,528. This patent describes a process of recovering ethylene glycol and dimethyl terephthalate from polyethylene terephthalate by dissolving the polyester resin in oligomers of the same monomers as are present in the polyester by passing super-heated methanol through the solution to depolymerize the polyester resin. Methanol, component monomers and impurities are then separated in a series of distillations. For ease of operation, the process of the '528 patent, preferably is performed at ambient pressure.

Gamble et al. U.S. Pat. No. 5,298,530 improves the process of the '528 patent by adding polyester resin to the system in a dissolver, where it is combined with reactor melt before the combination is transferred to the reactor for contact with super-heated methanol. In the reactor, polymers and oligomers are further depolymerized into component glycol and ester monomers, which are then recovered. This permits operating the dissolver at ambient pressure while operating the reactor at elevated pressure.

Toot et al. U.S. Pat. No. 5,414,022, optimizes the process of the '530 patent.

The processes described in this series of patents have numerous advantages. These include low cost, high efficiency, the ability to operate at relatively low pressure and the ability to use a variety of forms of polyester of varying degrees of cleanliness and purity.

However, when the process of the '528 patent is operated at ambient pressure, and the output of the reactor is cooled to commence separation of monomers, a three phase system is formed comprising Gaseous methanol, liquid ethylene glycol and solid dimethyl terephthalate. The low solubility of the dimethyl terephthalate in ethylene glycol results in its depositing on the surface of the cooling apparatus. This results in poor heat transfer, inefficient operation and the need for frequent cleaning.

The dissolver described in the '530 and '022 patents was developed, in part, to overcome this problem. The presence of the dissolver, which operates at ambient pressure, permits the reactor and the cooling apparatus to be operated at a sufficiently elevated pressure that a two phase system is maintained. In such a system the dimethyl terephthalate stays in solution until it is separated in a subsequent operation. Thus, it does not foul the cooling apparatus. Nevertheless, operating part of the recovery system at elevated pressure adds inconvenience and cost. Thus, it would be desirable to modify the apparatus and process so that the reactor and the recovery apparatus can be operated at ambient pressure, while minimizing fouling of the cooling apparatus.

SUMMARY OF THE INVENTION

We have found that fouling of the cooling apparatus can be minimized if a particular type of cooling apparatus is employed. In particular, when the cooling apparatus is a scraped surface heat exchanger, the deposition of dimethyl terephthalate on the surfaces of the cooling apparatus does not cause fouling since such a heat exchanger is equipped to remove the solids which collect.

The present invention provides a process for converting polyester to its component monomers. The apparatus used to carry out the process of the present invention is similar to that used in the '528 patent except that the output of the reactor is sent to a scraped surface heat exchanger for initial cooling. The apparatus described in the '530 patent can be employed as well, if found desirable, so long as it is operated at ambient pressure.

The present invention provides a process for depolymerizing polyester into its component monomers using apparatus comprising:

a reactor for depolymerizing polyester into monomer components, and a scraped surface heat exchanger for cooling the output of the reactor;

the process comprising performing, at ambient pressure, the steps of:

a) providing in the reactor a melt of polyester in oligomers of the polyester, b) passing super-heated methanol through the melt to depolymerize the polyester into component monomers which are removed from the reactor by the methanol vapor, c) cooling the output of the reactor in a scraped surface heat exchanger under conditions which cause monomer components to deposit on the surface of the heat exchanger, and d) removing the monomer components from the surface of the heat exchanger.

DETAILED DESCRIPTION OF THE INVENTION

Figure 1:
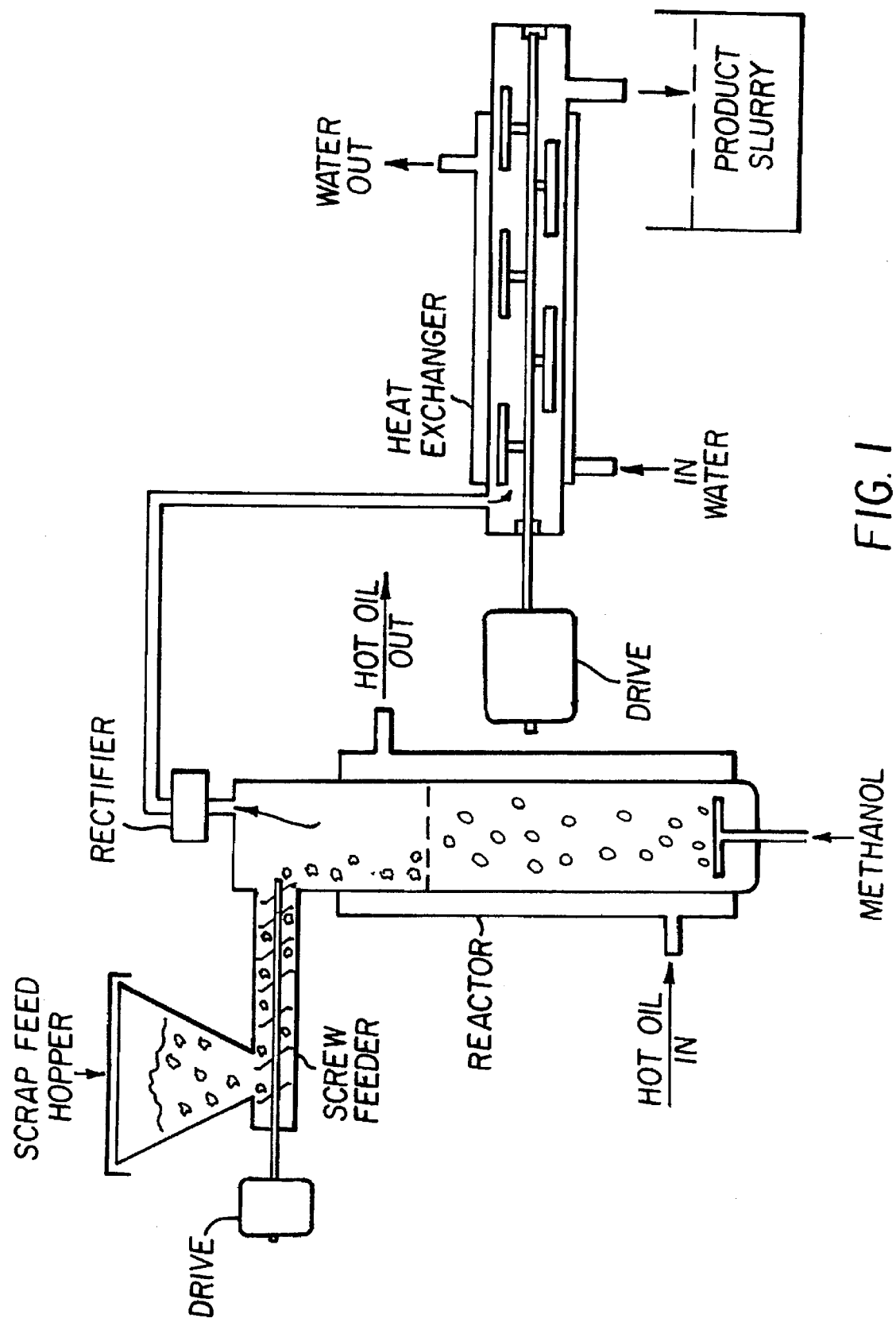
FIG. 1 is a schematic flow diagram illustrating apparatus that can be used to perform the inventive process.

In the apparatus shown in FIG. 1 polyethylene terephthalate in a suitable form and size is introduced into the reactor by any suitable means, such as the screw feeder shown.

Polyester introduced into the reactor contacts the melt already present. This initiates the depolymerization reaction and decreases the viscosity of the polyester. The reactor melt comprises methanol, low molecular weight polyesters, monomers, monohydric alcohol-ended oligomers, glycols, and dimethyl terephthalate and methylhydroxyethyl terephthalate.

There is added toward the bottom of the reactor super heated methanol vapor. Methanol is introduced into the reactor at a rate in the range of 2 to 6 parts by weight methanol per part polyester. The super-heated methanol vapor can be provided to the reactor by conventional means, such as a sparger.

The reactor shown is a vessel in which the melt forms a pool and through which the methanol is bubbled. The reactor is equipped with means for heating its contents to a temperature of up to about 305° C. Preferably the reactor contents are maintained at a temperature in the range of 240° to 260° C. Rather than being a pool reactor, the reactor can be of another suitable type, such as a staged column reactor, a counter current reactor or a cross flow reactor, as shown in our companion applications filed of even date herewith.

If desired, the polyester resin can be fed to a dissolver, as described in the '530 and '022 patents discussed above, before it is added to the reactor. In the dissolver the polyester is combined with melt drawn from the reactor and the combination is returned to the reactor. As indicated above, the dissolver operates at ambient pressure. Use of a dissolver facilitates removal of impurities introduced with the scrap in a way that does not require shutdown of the reactor.

There can be present in the reactor an ester exchange catalyst, such as zinc acetate. If used, catalyst is present in the range of 30 to 300 ppm polyester. Most preferably catalyst is employed in the range of 30 to 100 ppm polyester.

There also can be present in the reactor sufficient base to neutralize any acid formed from contaminants that may be carried in with the polyester scrap. If used, sufficient base is added to maintain the pH equivalent of the melt in the range of 7 to 10; preferably 7 to 8.

There is removed from the base of the reactor high boiling impurities and reaction by-products. Depending on the specific composition of this stream, it can be discarded or sent for recovery of specific components.

There is transferred from the reactor to the heat exchanger a vapor stream comprising methanol, glycols including ethylene glycol, diethylene glycol, and triethylene glycol, dimethyl terephthalate, dimethylisophthalate, cyclohexanedimethanol, and methylhydroxyethyl terephthalate.

If desired, a rectifier can be present between the reactor and the heat exchanger. The rectifier is operated at ambient pressure and a temperature in the range of 150° to 180° C. When operated in this way it separates higher boiling components, such as methylhydroxyethyl terephthalate, from the vapor stream exiting the reactor and returns them to the reactor in the form of a liquid. Presence of the rectifier simplifies the separation operation by removing higher boiling components that would condense with the dimethyl terephthalate and complicate its recovery.

The heat exchanger can be any of the scraped surface heat exchangers known in the art. There are shown in the following patent suitable designs for scraped surface heat exchangers that can be used in the process of this invention: U.S. Pat. Nos. 2,219,996, 2,868,830, 3,621,506, 3,836,573 and 4,315,541.

The heat exchanger can be operated under conditions that will separate the major portion of the dimethyl terephthalate from lower melting point compounds. Typically, the heat exchanger is operated at ambient pressure and a temperature in the range of 20° to 60° C.

There exits the heat exchanger a liquid slurry phase which comprises dimethyl terephthalate, ethylene glycol and methanol, and a vapor phase which comprises essentially all methanol. The products in these two phases can be recovered by techniques known in the art.

The following examples illustrate the invention.

EXAMPLE 1

The apparatus illustrated in FIG. 1. and described above was operated with the heat exchanger full of liquid, resulting in the complete condensation of the vapor stream from the reactor. The following were the conditions of operation of the reactor and heat exchanger:

| Reaction Conditions | |
| --- | --- |
| Reactor Melt Mass | 10 to 16 kg |
| Methanol Feed Rate | 200 ml/min |
| Scrap Feed Rate | adjusted to maintain constant melt mass |
| Reactor Temperature | 250° C. |
| Heat Exchanger Conditions | |
| Cooling Water Flow Rate | 9 gal/min |
| Cooling Water In | 21° C. |
| Cooling Water Out | 35° C. |
| Product Slurry | 63° C. |
| Scraper Speed | 40 rpm |

This apparatus was operated under the above conditions for 15 eight hour days without the heat exchanger failing. At the end of this period the heat transfer surfaces were examined and found to have only a slight build-up of dimethyl terephthalate.

EXAMPLE 2

The apparatus illustrated in FIG. 1. and described above was operated with the heat exchanger about ⅔ full of liquid, with a vapor layer above the liquid. The following were the conditions of operation of the reactor and heat exchanger:

| Reaction Conditions | |
| --- | --- |
| Reactor Melt Mass | 17 kg |
| Methanol Feed Rate | 150 ml/min |
| Scrap Feed Rate | adjusted to maintain constant melt mass |
| Reactor Temperature | 250° C. |
| Heat Exchanaer Conditions | |
| Cooling Water Flow Rate | 2 gal/min |
| Cooling Water In | 36° C. |
| Cooling Water Out | 60° C. |
| Product Slurry | 72° C. |
| Vapor Out | 71° C. |
| Scraper Speed | 40 rpm |

This apparatus was operated under the above conditions for a total of 35 hours over six days without the heat exchanger failing. Essentially steady state conditions were observed during periods of operation. The vapor stream exiting the heat exchanger was found to be essentially free of dimethyl terephthalate. The product slurry had dimethyl terephthalate crystals of a size distribution that facilitated draining and washing.

The invention has been described by reference to preferred embodiments, but it will be understood changes can be made to the apparatus and process steps specifically described herein within the spirit and scope of the invention.

What is claimed is:

1. A process for depolymerizing polyester into its component monomers using apparatus comprising:
    a reactor for depolymerizing polyester into monomer components, and
    a scraped surface heat exchanger for cooling the output of the reactor;

the process comprising performing, at ambient pressure, the steps of:
a) providing in the reactor a melt of polyester in oligomers of the polyester,
b) passing super-heated methanol through the melt to depolymerize the polyester into component monomers which are removed from the reactor by the methanol vapor,
c) cooling the output of the reactor in a scraped surface heat exchanger under conditions which cause monomer components to deposit on the surface of the heat exchanger, and
d) removing the monomer components from the surface of the heat exchanger.

2. The process of claim 1, wherein the polyester is added directly to the reactor.

3. The process of claim 1, in which the apparatus further comprise a dissolver connected to the reactor and the polyester is added to the dissolver, where it is combined with melt drawn from the reactor before the combined melt is returned to the reactor.

4. The process of claim 1, wherein the output of the reactor is passed directly to the heat exchanger.

5. The process of claim 1, where in the output of the reactor is passed to a rectifier where compounds having a boiling point higher than dimethyl terephthalate are separated and returned to the reactor.

* * * * *

UNITED STATES PATENT AND TRADEMARK OFFICE
CERTIFICATE OF CORRECTION

PATENT NO. : 5,654,470
DATED : August 5, 1997
INVENTOR(S) : Naujokas, et al

It is certified that error appears in the above-identified patent and that said Letters Patent is hereby corrected as shown below:

On the title page, after item [22] insert the following:
--[60] Provisional application No. 60/002,152, Aug. 11, 1995.--.

In column 1, line 3, after the title insert the following:
--This application claims the benefit of U. S. provisional application No. 06/002,152, filed Aug. 11, 1995.--.

Signed and Sealed this

Sixth Day of January, 1998

Attest:

BRUCE LEHMAN

*Attesting Officer*  *Commissioner of Patents and Trademarks*